United States Patent [19]
Sun et al.

[11] Patent Number: 5,925,800
[45] Date of Patent: Jul. 20, 1999

[54] CONVERSION OF OXYGENATES TO HYDROCARBONS WITH MONOLITH SUPPORTED NON-ZEOLITIC MOLECULAR SIEVE CATALYSTS

[75] Inventors: Hsiang-ning Sun, Houston, Tex.; Wenyih Frank Lai, Bridgewater, N.J.

[73] Assignee: Exxon Chemical Patents Inc., Houston, Tex.

[21] Appl. No.: 08/949,795

[22] Filed: Oct. 14, 1997

Related U.S. Application Data

[60] Provisional application No. 60/034,116, Dec. 31, 1996.
[51] Int. Cl.$^6$ ...................................................... C07C 1/00
[52] U.S. Cl. ............................. 585/640; 585/638; 585/639
[58] Field of Search .................. 585/638, 639, 585/640

[56] References Cited

U.S. PATENT DOCUMENTS

| | | | |
|---|---|---|---|
| 3,518,206 | 6/1970 | Sowards et al. ........................ | 252/446 |
| 4,440,871 | 4/1984 | Lok et al. ................................ | 502/214 |
| 4,524,234 | 6/1985 | Kaiser ..................................... | 585/638 |
| 4,677,243 | 6/1987 | Kaiser ..................................... | 585/638 |
| 5,413,975 | 5/1995 | Mueller et al. ........................... | 502/60 |

OTHER PUBLICATIONS

Zeolites, vol. 17, pp. 512–522 (1996).
Zeolites, vol. 17, pp. 212–222 (1996).

*Primary Examiner*—Glenn Caldarola
*Assistant Examiner*—In Suk Bullock
*Attorney, Agent, or Firm*—Bradley A. Keller

[57] ABSTRACT

The present invention provides a method for the conversion of oxygenates to olefins comprising exposing said oxygenates to a catalytic coating comprising a non-zeolitic molecular sieve catalyst coated on a support comprising inorganic materials, wherein said catalyst comprises in the range of from at least about 5 wt % of said support, under conditions effective to convert said oxygenates to olefins.

12 Claims, No Drawings

CONVERSION OF OXYGENATES TO HYDROCARBONS WITH MONOLITH SUPPORTED NON-ZEOLITIC MOLECULAR SIEVE CATALYSTS

This application claims priority to U.S. Provisional Patent Application No. 60/034,116, filed Dec. 31, 1996.

FIELD OF THE INVENTION

The present invention relates to supports for non-zeolitic molecular sieve catalysts, particularly monolithic supports for small pore silicoaluminophosphate catalysts, and to methods of using such catalysts to convert oxygenates to olefins.

BACKGROUND OF THE INVENTION

Light olefins, such as ethylene, serve as feeds for the production of numerous chemicals. Olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

Small pore molecular sieve catalysts, such as SAPO-34, are quite successful in converting methanol and dimethyl ether to olefins. However, methods are always needed for improving the performance of such small pore molecular sieve catalysts.

Some have suggested using low surface area supports (hereinafter "monolithic supports") containing zeolite catalysts. The use of a monolithic support could produce a relatively low pressure drop at low residence times and facilitate more uniform temperature distribution in the catalyst bed. However, zeolites are relatively hydrophilic and certain molecular sieves, particularly silicoaluminophosphate (SAPO) molecular sieves, are relatively hydrophobic. Materials that might be effective to bind a relatively hydrophilic zeolite catalyst to a monolithic support would not necessarily be effective to bind a relatively hydrophobic non-zeolitic catalyst to a monolithic support.

SUMMARY OF THE INVENTION

The present invention provides a method for the conversion of oxygenates to olefins comprising exposing said oxygenates to a catalytic coating comprising a non-zeolitic molecular sieve catalyst coated on a support comprising inorganic materials, wherein said catalyst comprises in the range of from at least about 5 wt % of said support, under conditions effective to convert said oxygenates to olefins.

DETAILED DESCRIPTION OF THE INVENTION

The invention involves the conversion of oxygenates to olefins using non-zeolitic molecular sieve catalysts carried on a monolithic support. Suitable molecular sieve catalysts include, but are not necessarily limited to, silicoaluminophosphates (SAPOs) and small pore aluminophospho oxides (ALPO's). Examples of suitable small pore ALPO's include, but are not necessarily limited to ALPO-20 and ALPO-25. Preferred molecular sieve catalysts are small pore silicoaluminophosphates (SAPOs), such as SAPO-34, SAPO 17, SAPO-18, SAPO-43, and SAPO44, and others which may be synthesized according to U.S. Pat. No. 4,440,871, incorporated herein by reference, and Zeolites, Vol. 17, pp. 512–522 (1996), incorporated herein by reference. Most preferred catalysts are SAPO-17, SAPO-18, and SAPO-34.

"Small pore" molecular sieve catalysts are defined as catalysts with pores having a diameter or pore size of less than about 5.0 Angstroms. Suitable catalysts have a pore size ranging from about 3.5 to about 5.0 Angstroms, preferably from about 4.0 to about 5.0 Angstroms, and most preferably from about 4.3 to about 5.0 Angstroms.

SAPO's have a three-dimensional microporous crystal framework of $PO_2^+$, $AlO_2^-$, and $SiO_2$ tetrahedral units. The chemical composition (anhydrous) is:

$$mR:(Si_xAl_yP_z)O_2$$

wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume in the pore system of the particular SAPO species involved, and "x", "y", and "z" represent the mole fractions of silicon, aluminum and phosphorus, respectively. "R" may be removed at elevated temperatures.

The "monolithic supports" of the present invention preferably are low surface area supports, or supports comprising materials with very little surface porosity. Low surface area materials have been difficult to coat with catalytic materials and have fewer sites at which catalytic activity can take place. Such materials include, but are not necessarily limited to glass, metals, and enamel, which are substantially devoid of surface porosity. Monolithic supports also may be made of materials which have minute surface porosity but which are not impregnated in the usual sense by treatment, e.g., with silica sols. Such materials include, but are not necessarily limited to porcelain, fused alumina, fused silica, mullite, beryl, zirconia, dense sintered alumina, chromia, spinel, magnesia, fused magnesia, and titania. The processes of the invention may be used to apply catalytic coatings to porous catalyst supports, but the real advantages are realized when the process is used to treat supports having a low surface area.

The size or form of the support is not important, and the support may be orientated or unorientated. The support may be in the shape of a honeycomb, a sponge, pellets, granules, spheres, bars, rods, tubes, rolls, spirals, screens, beads, coils, or any of the conventional shapes in the art. Suitable supports include those described in U.S. Pat. No. 3,518,206, incorporated herein by reference, either coated or uncoated with colloidal amorphous silica spherulites.

The monolithic support preferably should be washcoated with a preparation of alpha alumina, to smooth the surface and increase the surface area. Suitable washcoating may be prepared using a known slip casting process from an acid stabilized alpha-alumina, such as A16 SG, a 15 wt % acid stabilized alpha alumina available from Alcoa. The washcoated samples should be dried and sintered, preferably at about 1200° C. for about 24 hours.

A molecular-sieve containing slurry should be prepared by mixing a desired amount of molecular sieve catalyst with a binder material in a suitable solvent. Viscosifiers may be needed to prevent the slurry from running off the surface of the monolith after application. Any solvent may be used as long as the solvent does not adversely affect the binder and/or the molecular sieves, maintains the binder and molecular sieves in solution until after application to the monolith, and thereafter evaporates at relatively low temperatures—on the order of about 120° C.—and after a relatively short drying period—on the order of about 2 hours. A preferred solvent is water.

Effective binder materials include, but are not necessarily limited to colloidal alumina, (such as AL-20, available from Alcoa) and silica (such as LUDOX AS-40). A preferred binder is silica.

Suitable viscosifiers include, but are not necessarily limited to methyl cellulose (such as 20–213, a 20 wt % methyl cellulose) and polyethylene glycol (such as a 20 wt % 2,000 avg. MW PEG). Preferably, a combination of methyl cellulose and PEG should be used in an amount sufficient to raise the viscosity of the slurry to prevent runoff after application. The slurry also should include a suitable grinding media.

The mixture preferably should be milled and degassed to remove air bubbles. The alpha-alumina coated monolithic support then may be coated with the slurry, preferably using a known dip-coating process. Where the monolithic support is a honeycomb or a sponge-type structure, the excess slurry in the channels may be removed with compressed air.

The coated samples should be dried, preferably at about 120° C. for about 2 hours. The coating procedure should be repeated until a sufficient catalyst loading, preferably greater than about a 5 wt % catalyst loading, is achieved. Thereafter, the coated, dried samples should be calcined. A preferred rate of calcination is about 20° C. per hour for about 6 hours.

The monolithic supported catalyst preferably is used in a process for converting a starting material (feedstock) preferably comprising "oxygenates" to olefins. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety preferably should contain in the range of from about 1–10 carbon atoms and more preferably in the range of from about 1–4 carbon atoms. Representative oxygenates include, but are not necessarily limited to, lower straight chain or branched aliphatic alcohols, their unsaturated counterparts, and their nitrogen, halogen and sulfur analogues. Examples of suitable compounds include, but are not necessarily limited to: methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; diethyl sulfide; diethyl amine; ethyl chloride; formaldehyde; dimethyl carbonate; dimethyl ketone; acetic acid; n-alkyl amines, n-alkyl halides, n-alkyl sulfides having n-alkyl groups of in the range of from about 3–10 carbon atoms; and mixtures thereof. As used herein, the term "oxygenate" designates only the organic material used as the feed. The total charge of feed to the reaction zone may contain additional compounds such as diluents.

The conversion of feed to olefins preferably should be carried out in the vapor phase. Preferably, the feedstock should be contacted in the vapor phase in a reaction zone with the defined monolithically supported molecular sieve catalyst at effective process conditions so as to produce the desired olefins, i.e., an effective temperature, pressure, WHSV (Weight Hourly Space Velocity) and, optionally, an effective amount of diluent, correlated to produce olefins. Alternately, the process may be carried out in a liquid phase. When the process is carried out in the liquid phase, different conversion rates and selectivities of feedstock-to-product may result.

The temperature employed in the conversion process may vary over a wide range depending, at least in part, on the selected catalyst. Although not limited to a particular temperature, best results will be obtained if the process is conducted at temperatures in the range of from about 200° C. to 700° C., preferably in the range of from about 250° C. to 600° C., and most preferably in the range of from about 300° C. to 500° C. Lower temperatures generally result in lower rates of reaction, and the formation of the desired light olefin products may become markedly slow. However, at higher temperatures, the process may not form an optimum amount of light olefin products.

Light olefin products will form—although not necessarily in optimum amounts—at a wide range of pressures, including but not limited to autogeneous pressures and pressures in the range of from about 0.1 kPa to about 100 MPa. A preferred pressure is in the range of from about 6.9 kPa to about 34 MPa, most preferably in the range of from about 48 kPa to about 0.34 MPa. The foregoing pressures are exclusive of inert diluent, if any is present, and refer to the partial pressure of the feedstock as it relates to oxygenate compounds and/or mixtures thereof. Pressures outside of the stated ranges may operate and are not excluded from the scope of the invention. Lower and upper extremes of pressure may adversely affect selectivity and/or conversion rates.

The process should be continued for a period of time sufficient to produce the desired olefin products. The reaction time may vary from seconds to a number of hours. The reaction time is largely determined by the reaction temperature, the pressure, the catalyst selected, the weight hourly space velocity, the phase (liquid or vapor), and the selected process design characteristics.

A wide range of weight hourly space velocity (WHSV) for the feedstock will function in the present invention. The WHSV generally should be in the range of from about 0.01 $hr^{-1}$ to about 500 $hr^{-1}$, preferably in the range of from about 0.1 $hr^{-1}$ to about 200 $hr^{-1}$, and most preferably in the range of from about 0.5 $hr^{-1}$ to about 100 $hr^{-1}$. The catalyst may contain other materials which act as inerts; therefore, the WHSV is calculated on the weight basis of methanol or dimethyl ether and catalyst.

The feed may contain one or more inert diluents in an amount in the range of from about 1–99 molar percent, based on the total number of moles of all feed and diluent components fed to the reaction zone (or catalyst). Diluents which may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Preferred diluents are water and nitrogen.

The process may be carried out in a batch, semi-continuous, or continuous fashion. The process may use a single reaction zone or a number of reaction zones arranged in series or in parallel. The process may be intermittent or continuous in an elongated tubular zone or a number of such zones. When multiple reaction zones are used, one or more of the monolithically supported catalysts advantageously may be used in series to provide for a desired product mixture.

The following examples illustrate, but do not limit, the present invention.

EXAMPLE 1

SAPO-34 molecular sieve catalyst was obtained from UOP, Des Plaines, Ill., disclosed in U.S. Pat. No. 4,440,871, incorporated herein by reference.

EXAMPLE 2

Standard cordierite honeycombs (#9475) with 400 channels/m$^2$, a ⅓ inch outside diameter, and a length of 9 inches, were obtained. The honeycombs first were wash-coated with alpha alumina, to smooth the surface and increase the surface area. The washcoating was prepared from an acid stabilized alpha-alumina (A16 SG, obtained from Alcoa) using a slip casting process. The washcoated samples were dried and sintered at 1200° C. for 24 hours.

A molecular-sieve containing slurry was prepared by adding to a 500 ml polyethylene bottle the following: 9 g of the SAPO-34 molecular sieve catalyst obtained in Example 1; 60 g water; 30 g colloidal alumina (AL-20, obtained from Alcoa); 45 g of methyl cellulose (20–213, 2 wt %); 2 ml of PEG (MW=2,000, 20 wt %); and, grinding media.

The mixture was milled overnight and degassed to remove air bubbles. The alpha-alumina coated honeycombs then were coated with the slurry using a dip-coating process. The excess slurry in the channels of the honeycombs was removed with compressed air. The coated samples then were dried at about 120° C. for 2 hours. The coating procedure was repeated two or three times, until greater than 5 wt % loading of catalyst was achieved. After all of the coating and drying steps were completed, the samples were calcined at a rate of 20° C. per hour for 6 hours.

A 1:1 mixture of methanol and water is contacted with the catalyst in a catalytic zone at a temperature of about 350° C., at a pressure of about 34 kPa (5 psia), and at a weight hourly space velocity of about 1.3 hr$^{-1}$. The conversion of methanol to carbon dioxide and hydrogen is approximately 30%. Only small amounts of methane, CO, and dimethyl ether are found in the product.

EXAMPLE 3

The procedures of Example 2 were repeated substituting the colloidal alumina in the slurry with 15 g of LUDOX AS-40.

A 1:1 mixture of methanol and water is contacted with the catalyst in a catalytic zone at a temperature of about 350° C., at a pressure of about 34 kPa (5 psia), and at a weight hourly space velocity of about 1.3 hr$^{-1}$. The conversion of methanol to carbon dioxide and hydrogen is approximately 30%. Only small amounts of methane, CO, and dimethyl ether are found in the product.

EXAMPLE 4

The procedures of Example 2 were repeated substituting the honeycomb monolithic support with alumina form support called RETICEL, obtained from Hi-Tech Ceramics.

A 1:1 mixture of methanol and water is contacted with the catalyst in a catalytic zone at a temperature of about 350° C., at a pressure of about 34 kPa (5 psia), and at a weight hourly space velocity of about 1.3 hr$^{-1}$. The conversion of methanol to carbon dioxide and hydrogen is approximately 30%. Only small amounts of methane, CO, and dimethyl ether are found in the product.

Persons of ordinary skill in the art will recognize that many modifications may be made to the present invention without departing from the spirit and scope of the present invention. The embodiments described herein are meant to be illustrative only and should not be taken as limiting the invention, which is defined in the following claims.

We claim:

1. A method for the conversion of oxygenates to olefins comprising exposing said oxygenates to a catalytic coating comprising a non-zeolitic molecular sieve catalyst and an amount and distribution of a binder which is effective to bind the non-zeolitic molecular sieve catalyst to a support comprising inorganic materials, wherein said binder comprises a material selected from the group consisting of colloidal alumina, silica, and a combination thereof and wherein said catalyst comprises between at least about 5 wt % of said support, under conditions effective to convert said oxygenates to olefins.

2. The method of claim 1 wherein said conditions comprise
   a temperature in the range of from about 200° C. to 700° C.;
   a pressure in the range of from about 0.1 kPa and about 100 MPa; and
   a weight hourly space velocity of in the range of from about 0.01 hr$^{-1}$ to about 500 hr$^{-1}$.

3. The method of claim 1 wherein said conditions comprise
   a temperature in the range of from about 250° C. to 600° C.;
   a pressure in the range of from about 6.9 kPa to about 34 MPa; and
   a weight hourly space velocity of in the range of from about 0.1 hr$^{-1}$ to about 200 hr$^{-1}$.

4. The method of claim 1 wherein said conditions comprise
   a temperature in the range of from about 300° C. to 500° C.;
   a pressure in the range of from about 48 kPa to about 0.34 MPa; and
   a weight hourly space velocity of in the range of from about 0.5 hr$^{-1}$ to about 100 hr$^{-1}$.

5. The method of claim 1 wherein said non-zeolitic molecular sieve catalyst comprises a silicoaluminophosphate molecular sieve catalyst.

6. The method of claim 1 wherein said non-zeolitic molecular sieve catalyst comprises a small pore non-zeolitic molecular sieve catalyst.

7. The method of claim 5 wherein said non-zeolitic molecular sieve catalyst comprises a small pore silicoaluminophosphate molecular sieve catalyst.

8. The method of claim 1 wherein said oxygenates are selected from the group consisting of aliphatic alcohols, ethers, carbonyl compounds, and compounds comprising hetero-atoms.

9. The method of claim 8 wherein said aliphatic alcohols comprise an aliphatic moiety having in the range of from about 1–10 carbon atoms.

10. The method of claim 8 wherein said aliphatic alcohols comprise an aliphatic moiety having in the range of from about 1–4 carbon atoms.

11. The method of claim 1 wherein said oxygenates are selected from the group consisting of: lower straight chain and branched aliphatic alcohols; unsaturated counterparts thereof; and, nitrogen, halogen and sulfur analogues thereof.

12. The method of claim 1 wherein said oxygenates are selected from the group consisting of: methanol; ethanol; n-propanol; isopropanol; $C_4$–$C_{10}$ alcohols; methyl ethyl ether; dimethyl ether; diethyl ether; di-isopropyl ether;

methyl mercaptan; methyl sulfide; methyl amine; ethyl mercaptan; diethyl sulfide; diethyl amine; ethyl chloride; formaldehyde; dimethyl carbonate; dimethyl ketone; acetic acid; n-alkyl amines, n-alkyl halides, and n-alkyl sulfides comprising n-alkyl groups having in the range of from about 3–10 carbon atoms; and, mixtures thereof.

* * * * *